(12) United States Patent
Shoenfeld et al.

(10) Patent No.: US 10,678,901 B2
(45) Date of Patent: Jun. 9, 2020

(54) MEDICATIONS OR ANESTHESIA CART OR CABINET WITH FACIAL RECOGNITION AND THERMAL IMAGING

(71) Applicants: Norman A. Shoenfeld, Cypress, TX (US); Bryan Scott Sangalli, Houston, TX (US)

(72) Inventors: Norman A. Shoenfeld, Cypress, TX (US); Bryan Scott Sangalli, Houston, TX (US)

(73) Assignee: S&S X-ray Products, Inc., Houston, TX (US)

( * ) Notice: Subject to any disclaimer, the term of this patent is extended or adjusted under 35 U.S.C. 154(b) by 96 days.

(21) Appl. No.: 16/032,521

(22) Filed: Jul. 11, 2018

(65) Prior Publication Data

US 2020/0019681 A1  Jan. 16, 2020

(51) Int. Cl.
| | | |
|---|---|---|
| *G06F 21/32* | (2013.01) | |
| *G06K 9/00* | (2006.01) | |
| *A61G 12/00* | (2006.01) | |
| *A61B 50/13* | (2016.01) | |
| *A61B 50/10* | (2016.01) | |
| *A61B 50/18* | (2016.01) | |

(52) U.S. Cl.
CPC ............ *G06F 21/32* (2013.01); *A61B 50/13* (2016.02); *A61G 12/001* (2013.01); *G06K 9/00288* (2013.01); *A61B 2050/105* (2016.02); *A61B 2050/185* (2016.02)

(58) Field of Classification Search
CPC ................ A61G 12/001; A61B 5/1176; A61B 2050/105; A61B 2050/185; A61B 50/13; G06F 21/32; G06F 21/44; G06K 9/00288

USPC ......................................................... 382/118
See application file for complete search history.

(56) References Cited

U.S. PATENT DOCUMENTS

| | | | |
|---|---|---|---|
| 7,856,558 B2 | 12/2010 | Martin et al. | |
| 8,917,914 B2 | 12/2014 | Zheng | |
| 9,202,105 B1 | 12/2015 | Wang et al. | |
| 9,607,138 B1 | 3/2017 | Baldwin et al. | |
| 10,453,572 B1* | 10/2019 | Brooks | G16H 40/63 |
| 2002/0136435 A1 | 9/2002 | Prokoski | |
| 2003/0229499 A1* | 12/2003 | Von Bosse | G10L 15/26 704/275 |
| 2004/0017934 A1 | 7/2004 | Kocher | |
| 2005/0062238 A1* | 3/2005 | Broadfield | A61B 50/13 280/1 |
| 2006/0139148 A1* | 6/2006 | Faro | G07C 9/00103 340/5.73 |
| 2010/0045809 A1 | 2/2010 | Packard | |
| 2010/0228392 A1* | 9/2010 | Braun | A61G 12/001 700/242 |
| 2010/0289641 A1 | 11/2010 | Kates | |
| 2012/0257800 A1 | 10/2012 | Zheng | |
| 2012/0272576 A1* | 11/2012 | Van Tassell, III | E05F 15/641 49/70 |

(Continued)

*Primary Examiner* — Daniel G Mariam
(74) *Attorney, Agent, or Firm* — Bernhard P. Molldrem, Jr.

(57) ABSTRACT

A cabinet or cart has at least one limited-access drawer or compartment and employs facial recognition (FR) to permit an authorized user to access the limited-access drawer or compartment. A visible light image of the user and a thermal image of the user are taken simultaneously or nearly simultaneously, with the thermal image serving to confirm the validity of the FR and authenticate the user's identity.

9 Claims, 2 Drawing Sheets

(56) References Cited

U.S. PATENT DOCUMENTS

| | | |
|---|---|---|
| 2013/0169760 A1 | 7/2013 | Watts |
| 2013/0321641 A1 | 12/2013 | McManus et al. |
| 2014/0184038 A1* | 7/2014 | Shoenfeld ........... G07C 9/00111 |
| | | 312/209 |
| 2016/0089303 A1* | 3/2016 | Latorraca ................ G07F 11/62 |
| | | 312/209 |
| 2017/0195548 A1 | 7/2017 | McManus et al. |
| 2019/0268575 A1* | 8/2019 | Leow ............... H04N 5/232411 |

* cited by examiner

MEDICATIONS OR ANESTHESIA CART OR CABINET WITH FACIAL RECOGNITION AND THERMAL IMAGING

BACKGROUND OF THE INVENTION

This invention relates to medications carts, cabinets, and items providing storage and access to patient pharmaceuticals and other items to be administered in a hospital, transitional care facility, clinic, or other health care facility where administration of the materials must be managed and controlled. The invention also concerns related carts and cabinets from which controlled or potentially dangerous materials, e.g., anesthetics, are to be dispensed and/or administered.

Currently, to gain access to one of these carts or cabinets, an authorized user has to enter a user ID, which can be a machine readable code on a badge or card, or may be a code that the user enters at a keyboard. To gain access to more secure compartments in the cart or cabinet, e.g., narcotics or anesthetic storage, the user has to also enter a narcotics access code. Access can take some time to accomplish, as it first involves activating a touch screen and then pushing the digits for each access code, followed by pushing the "enter" key and then selecting which drawer or compartment, and then waiting for a motor to turn to open the compartment door or unlock a drawer. This procedure can consume considerable time over the course of a day.

One improvement to this method of gaining authorized access would be the use of facial recognition (FR), initiated by speaking an "activation word" which is recognized by the electronics on the cart or cabinet to start the FR access procedure. For example, the user may speak "Door One" or "Door Two", or press a specific key or button to access Door One or Door Two of the cabinet or cart. In this FR process, an onboard camera takes a picture of the user attempting access, and the picture is compared with the image data in a digital stored library of photographs of authorized users. The picture taken by the onboard camera is compared with these stored pictures using e.g. a vectorization process, and if there is a match, the specific door or drawer or compartment is unlocked or opened. All data, including the image data, can be stored to create an audit trail of all access attempts, successful or not. Typically, what is stored is the vectorized image data, although optionally the actual image can be stored, at least for the users who are denied access. An optional light or flash can be employed in low light environments to ensure the FR photograph is of sufficient quality.

The above technique has been tested, and can work well with good sensitivity and specificity. However, the facial recognition system and be tricked or "fooled" by using a good photograph of an authorized user and presenting that to the camera used for facial recognition. A portrait photo taken on a smart cellular phone, i.e., a "selfie", can also fool the FR system.

One possible solution to this flaw in the FR system could be to combine a current sign-in procedure, such as a code entry, with facial recognition, which has the advantage that simply having a photograph of an authorized user, or having only the authorized user's ID code, would not be sufficient, as one would need both to access the cabinet. Retinal or thumbprint authentication could also be combined with facial recognition, but this would also add time to the procedure. These are better solutions than FR alone, but can still be tricked and also the existing sign-in and code entry procedures slow the validation process down, as discussed earlier.

OBJECTS AND SUMMARY OF THE INVENTION

It is an object of the present invention to provide a quick but secure technique for an authorized user, e.g., nurse, physician or pharmacist, to access a limited-access drawer or compartment in a cabinet or cart, but which avoids the drawbacks mentioned above.

It is another object to provide a technique for accessing a given drawer or compartment in a medical or hospital cart or cabinet that can provide access history, that is, an audit trail of persons accessing and attempting access to the cabinet or cart, including visual images of the person attempting access.

It is more specific object to provide a check on authenticity of the image or the person attempting access and to defeat an attempt to trick or fool the system.

In accordance with an aspect of this invention, the medications or anesthesia cart or cabinet has a cabinet housing, with a computer control arrangement mounted on or in the cabinet and including a computer processor. At least one locking compartment in the cabinet is provided for limited access only by authorized persons, and includes an electro-mechanical lock coupled to the computer processor. A first camera on the cabinet is oriented to obtain an image of a user of the cabinet or cart and is adapted for providing a normal, visible-light image of the user to the computer processor; and a second camera on said the is oriented to obtain a thermal image of the user and is adapted for providing the thermal image data to the computer processor. An optional voice recognition facility in the computer processor has an audio pickup adapted to receive an audible spoken command of the user, and a speech recognition functionality in the computer processor which is adapted to receive the audible spoken command of said user and recognize and interpret such spoken command whereby a predetermined spoken command is operative to open the at least one locking compartment.

The computer processor is further operative to compare data in the visible image and data in the thermal image sufficient to ensure that both the visible and thermal images represent the face of an authorized user, such that access and opening of the electromagnetic lock to unlock the at least one locking compartment occurs only when the visible images and thermal images both represent the face of a given authorized user, but when the visible and thermal images do not both represent the face of such authorized user the discrepancy between the visible and thermal images is operative to block the at least one locking compartment from opening.

Favorably, the computer processor memory contains a data base or library of image information corresponding to a plurality of authorized users, and the computer processor is operative to unlock the at least one locking compartment when visible and thermal images match the image information of one of the authorized users.

The voice recognition (VR) facility of the computer processor may also include in its memory speech patterns of a plurality of authorized users, may be operative to unlock the at least one locking compartment only when the user's spoken commands match a speech pattern of an authorized user as stored in the computer memory. However, many VR systems require Internet access, and would be problematic to use, out of privacy concerns.

In a favorable embodiment, the first (i.e., visible light) and second (thermal-imaging) cameras are operative to obtain the visual and thermal images, respectively, of the user of the cart or cabinet upon the computer processor receiving a spoken command to open the at least one locking compartment. The first and second cameras are most favorably operated simultaneously, or nearly simultaneously, i.e., sequentially within a brief predetermined length of time that is less than a time required to substitute a false image of a face for the user for either of said first or second cameras. This period is one second or less and typically a matter of only a few milliseconds. The thermal imaging camera can be actuated before the visible imaging camera without departing from the principles of the invention.

The cart or cabinet may have at least a first locking compartment and a second locking compartment, and may have several such limited-access drawers or compartments.

The medications or anesthesia cart or cabinet's computer processor memory may contain speech patterns of a first group of authorized users which are authorized access to the first locking compartment and speech patterns of a second group of authorized users which are authorized access to the second locking compartment, and so on for individual locking compartments or for groups of such locking compartments.

These and many other objects, features, and advantages of the medications or anesthesiology cart or cabinet will become apparent from the ensuing detailed description which is to be considered in connection with the accompanying Drawing.

DETAILED DESCRIPTION OF A PREFERRED EMBODIMENT

Figure 1:
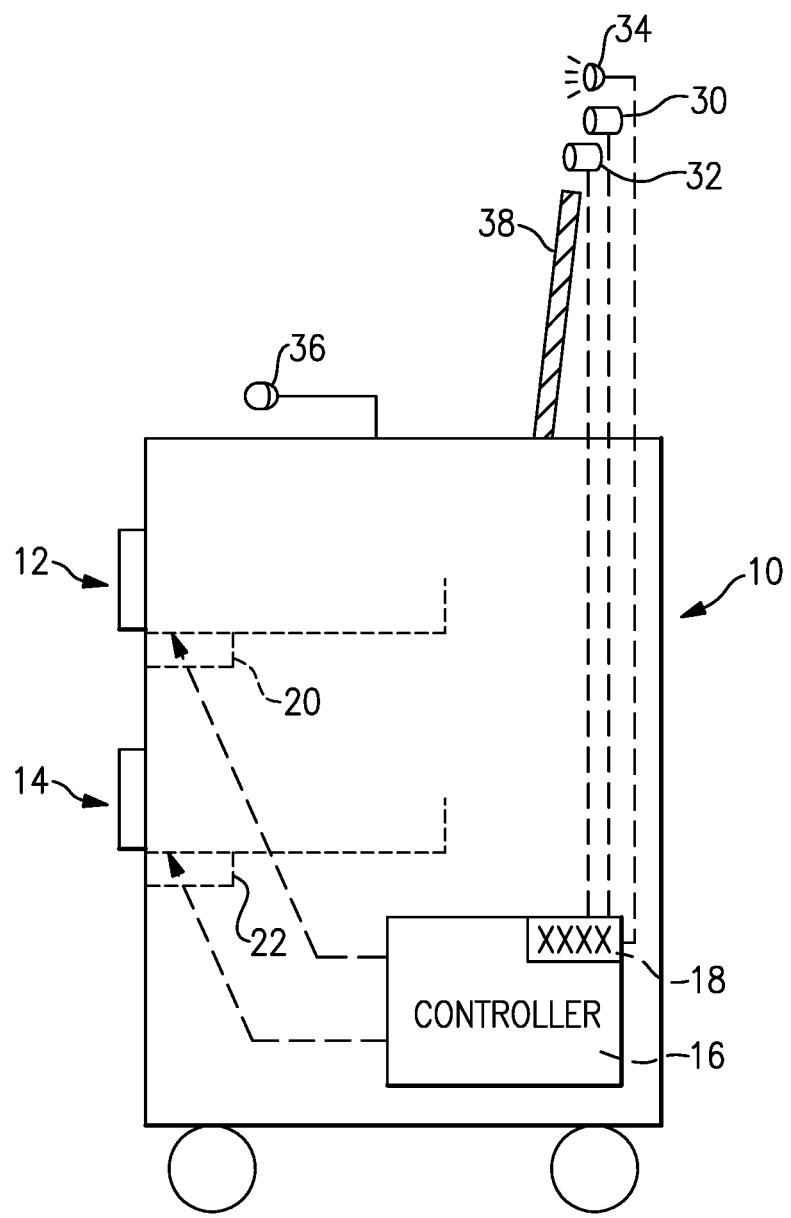
FIG. 1 is a schematic view of a cart or cabinet according to an embodiment of this invention.

With reference to the Drawing, FIG. 1 schematically illustrates a medications cabinet 10, here shown with rollers or wheels, but which can be stationary as an in-room dispensing cabinet or as a mobile cabinet or cart, and which may be for dispensing patient medications or for anesthesiology use. The cabinet is generally in the form of an enclosure, here with a first drawer 12 and a second drawer 14, which may otherwise be embodied as locking compartments. The drawers or compartments need to be opened for access to their contents by a user, typically a nurse. The drawers 12 and 14 are normally kept locked and are unlocked only to provide access for individual authorized care-givers. A computer-based controller 16 is here shown within the cabinet 10, and contains a face-recognition software functionality 18 for processing digital images of a user's face taken in visible light and one taken in infrared as a thermal image.

A controlled drawer lock 20 is associated with the first drawer 12 and another controlled drawer lock 22 is associated with the second drawer 14.

Here shown at a position above the cabinet 10 and facing in a proximal direction (towards the user) are a visible light imaging camera 30, a thermal imaging camera 32 and a lamp 34 aimed at the location of the user's head for providing optional illumination, as needed. Also shown above the cabinet 10 are a microphone or sound pick-up 36 and a viewing screen or monitor 38, which may be a touch-screen or may be associated with a keyboard.

While the drawing shows this embodiment having wheels or rollers at the base of the cabinet 10, it should be recognized that this invention can be equally applicable to a fixed, in-room cabinet or in a larger pharmaceutical cabinet located in a medications room.

In practice, the controlled drawers can be opened when an authorized user gives a verbal command, such as "open drawer one" or perhaps simply "drawer one". The user would be standing at a predetermined location in front of the cabinet 10 when giving the oral command, and the controller 16 would be triggered to initiate the facial recognition (FR) procedure, first taking images of the user using the visible light camera 30 and the thermal imaging camera 32. These images can be taken simultaneously or sequentially within a very short interval (e.g., less than roughly one second), short enough so that a simulated thermal image phonograph cannot be substituted for photograph of an authorized user if someone were to attempt to fool or trick the system and open drawer one or drawer two. Alternatively, the visual and thermal authentication process can be initiated any time a person attempts to open a drawer, for example, by pressing a key or button to open drawer one or drawer two, or by placing a hand on the respective drawer.

In the event that the camera 30 does not present a clear enough image of the user's face, a re-take is initiated, also energizing the flash or lamp 34.

Figure 2:
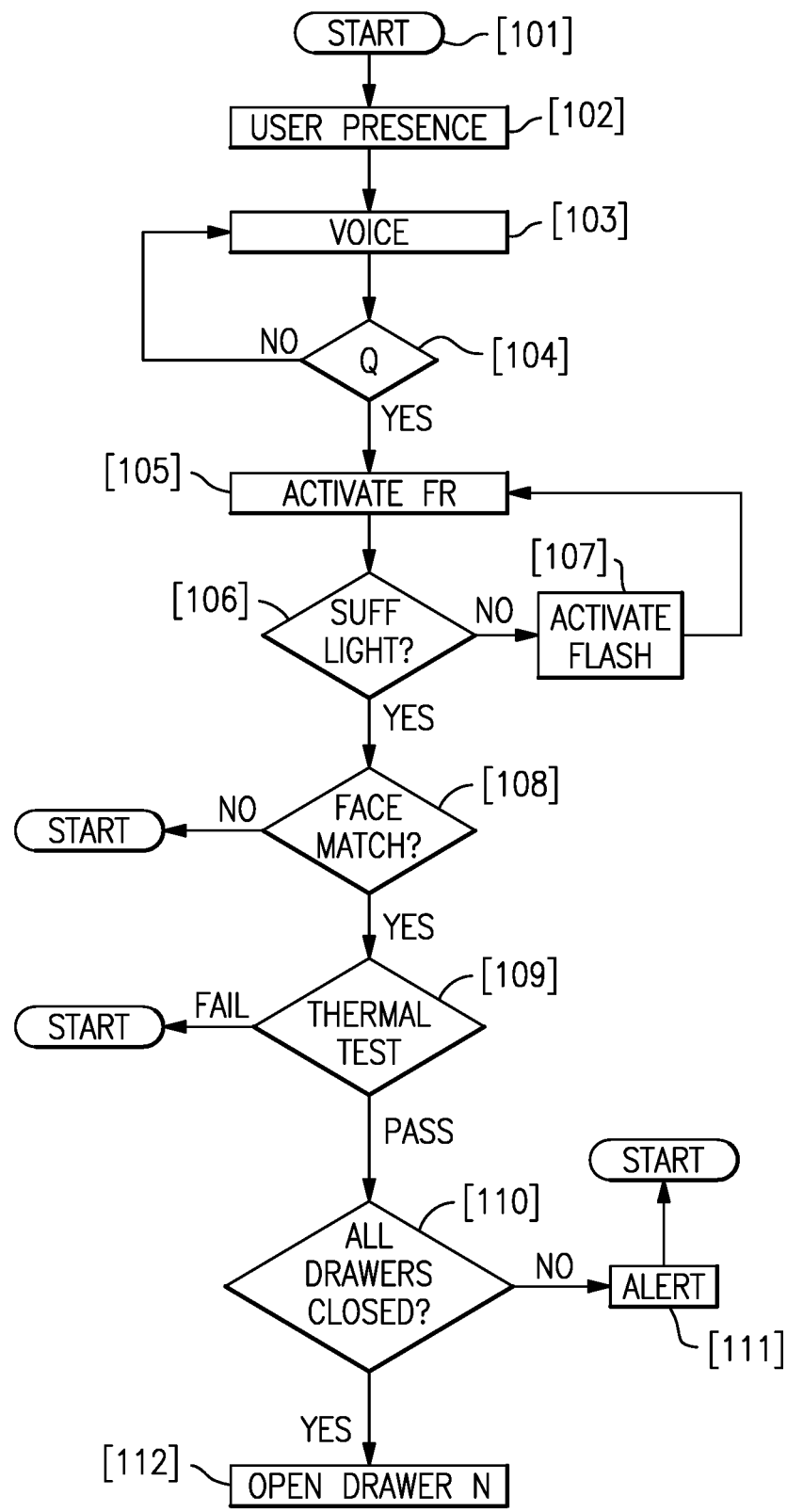
FIG. 2 is a logic chart explaining the process employed in this embodiment.

The process employed by the controller 16 can be described with reference to the logic chart of FIG. 2. When the cart or cabinet controller is turned on, the unit commences a start sequence [101] and then remains in the start or ready state, awaiting detection of a user's presence [102] at the front of the cart or cabinet. In this example the audio pickup 36 supplies audio to the controller 16, which, as shown in block [103] detects a user's voice commands, and detects when the user states a proper command, such as "open drawer one." As shown, a decision module [104] returns the process to listen mode for voice commands as at block [103] if the voice command is not present, but proceeds to activate the facial recognition procedure as in block [105]. This procedure actuates the camera or visual spectrum imager 30 to capture an image of the face of the user. If the image is dim or difficult to process, usually due to insufficient light, the flash or lamp 34 is energized (block [107]), and the facial recognition procedure is repeated, taking and analyzing a new image. The image is compared with a library of face image data for authorized users, e.g., assigned staff nurse and pharmacy personnel, and if there is a match with an authorized user's face (block [108]) the procedure continues to test the visual light image with the thermal (or infrared) image data obtained from camera 32 (block [109]). If there is no face match found the procedure returns to the start or ready state.

When the thermal image data comports with the facial recognition image data, confirming that the images are not those of a photograph of a face or a cell phone screen, the facial recognition test is deemed to have been passed, but in other events the procedure returns to the start or ready state. The state of the drawers 12 and 14 is checked to ensure they are both in their closed and/or locked state (block [110]). If they are not all closed, an alert is sounded [111] and the procedure returns to the initial start or ready state. If the system shows the drawers 12 and 14 are closed and locked, then the controller 16 triggers the appropriate one of the drawer controls 20 or 22 to unlock the associated drawer. When the cabinet compartment or drawer has been accessed and the compartment or drawer closed by the user, the procedure again returns to the start or ready mode.

In summary, when the user wants to open a compartment, either by using an "activation word" such as "open drawer one", or has pushed a button specific to the drawer number one, the FR authentication procedure is initiated. The camera 30 takes a picture of the person standing at the front of the cart or cabinet 10. The picture is compared, favorably using a vectorization process, with a database or library of stored photographs of the authorized users. If there is a match, because the facial recognition software can be "fooled" by using a good photograph of an authorized user, the visual-light image is checked against image data from the second or thermal imaging camera 32, that image data having been taken of the same subject in the same place at substantially the same time (within a fraction of a second). If the authorized user is actually present, then the thermal image from the thermal imaging camera 32 should match the expected image data obtained from the visual light image from camera 30. The comparison can be made with previously stored thermal image data of that user, or can match the hot and cool portions of the thermal image with features such as eyes, nose, cheeks, chin of the user's visual light face image. If a live person is verified by the thermal image (which will not match up if the thermal image is that of a photograph or a picture displayed on a screen) then the specific bin or compartment or drawer can be opened.

All activities involved with accessing the locked drawers on the medications cart or cabinet are stored and an audit trail is created.

Within the concept of this invention, it would be possible also to add facial recognition and thermal imaging to other sign-in systems, i.e., a smart ID or a personal code or PIN, rather than using voice recognition and speech recognition to initiate access by an authorized user.

An over-ride can be employed in some instances where the thermal image of the actual authorized user may not provide access, e.g. where the user has been in an unusually hot or cold environment such that the thermal image profile does not match. In that case the user would enter the user ID and the required passwords manually on a keyboard to access the cart or cabinet. Optionally, a finger print scan, retinal scan, etc. can be used for secondary verification.

While the invention has been discussed in reference to a preferred embodiment, the invention is not limited to that embodiment and it should be recognized that many modifications and variations are possible without departing from the scope and spirit of this invention, as defined in the appended Claims.

What is claimed is:

1. A medications or anesthesia cart or cabinet comprising:
   a cabinet;
   a computer control arrangement mounted on or in said cabinet and including a computer processor;
   at least one locking compartment in said cabinet including an electro-mechanical lock coupled to said computer processor;
   a first camera on said cabinet oriented to obtain an image of a user of said cart and adapted for providing a visible light image of said user to said computer processor;
   a second camera on said cabinet oriented to obtain a thermal image of said user of said cabinet and adapted for providing said thermal image to said computer processor;
   sensor means on or in said cabinet and coupled to said computer control arrangement to receive a user command to commence opening said at least one locking compartment;
   said computer processor being further operative in response to the user command from said sensor first to compare data in said visible image with stored facial recognition data for at least one authorized user, and then if the visual image matches the stored facial recognition data for the at least one authorized user, determining whether data in said thermal image is sufficient to ensure that the thermal image is consistent with an image of a human face, and permitting said electromagnetic lock to unlock said at least one locking compartment when the visible image corresponds to the face of a given one of said at least one authorized user and said thermal image is consistent with the image of a human face, but operative to block the at least one locking compartment from opening when the visible image does not correspond with stored data that represents the face of said at least one authorized user or when the thermal image is not consistent with the image of a human face.

2. The medications or anesthesia cart according to claim 1, wherein said computer processor includes a memory containing image information corresponding to a plurality of authorized users, and is operative to unlock said at least one locking compartment when said visible image matches the stored image data for any of said plurality of authorized users.

3. The medications or anesthesia cart according to claim 1, wherein said sensor means to receive a user command includes an audio pickup adapted to receive an audible spoken command of the user, and a speech recognition functionality in said computer processor adapted to receive said audible spoken command of said user and recognize and interpret said spoken command and wherein a predetermined spoken command is operative to commence opening said at least one locking compartment.

4. The medications or anesthesia cart according to claim 3, wherein the speech recognition facility of said computer processor includes a memory containing speech patterns of a plurality of authorized users, and is operative to commence opening said at least one locking compartment only when the spoken commands match a speech pattern of an authorized user stored in said memory.

5. The medications or anesthesia cart according to claim 4, wherein said at least one locking compartment includes at least a first locking compartment and a second locking compartment.

6. A medications or anesthesia cart or cabinet comprising:
   a cabinet;
   a computer control arrangement mounted on or in said cabinet and including a computer processor;
   at least one locking compartment in said cabinet including an electro-mechanical lock coupled to said computer processor;
   a first camera on said cabinet oriented to obtain an image of a user of said cart and adapted for providing a visible light image of said user to said computer processor;

a second camera on said cabinet oriented to obtain a thermal image of said user of said cabinet and adapted for providing said thermal image to said computer processor;
means on or in said cabinet to receive a user command to commence opening said at least one locking compartment;
said computer processor being further operative to process data in said visible image and data in said thermal image sufficient to ensure that both images represent the face of an authorized user, and permitting said electromagnetic lock to unlock said at least one locking compartment when the visible image represents the face of a given authorized user, but operative to block the at least one locking compartment from opening when the thermal image does not correspond to a human face;
wherein said sensor means to receive a user command includes an audio pickup adapted to receive an audible spoken command of the user, and a speech recognition functionality in said computer processor adapted to receive said audible spoken command of said user and recognize and interpret said spoken command and wherein a predetermined spoken command is operative to commence opening said at least one locking compartment,
wherein the speech recognition facility of said computer processor includes a memory containing speech patterns of a plurality of authorized users, and is operative to commence opening said at least one locking compartment only when the spoken commands match a speech pattern of an authorized user stored in said memory wherein said at least one locking compartment includes at least a first locking compartment and a second locking compartment;
and wherein said memory contains speech patterns of a first group of authorized users which are authorized access to said first locking compartment and speech patterns of a second group of authorized users which are authorized access to said second locking compartment.

7. A medications or anesthesia cart or cabinet comprising:
a cabinet;
a computer control arrangement mounted on or in said cabinet and including a computer processor;
at least one locking compartment in said cabinet including an electro-mechanical lock coupled to said computer processor;
a first camera on said cabinet oriented to obtain an image of a user of said cart and adapted for providing a visible light image of said user to said computer processor;
a second camera on said cabinet oriented to obtain a thermal image of said user of said cabinet and adapted for providing said thermal image to said computer processor;
means on or in said cabinet to receive a user command to commence opening said at least one locking compartment;
said computer processor being further operative to compare data in said visible image and data in said thermal image sufficient to ensure that both images represent the face of an authorized user, and permitting said electromagnetic lock to unlock said at least one locking compartment when the visible image represents the face of a given authorized user, but operative to block the at least one locking compartment from opening when thermal image does not correspond to a human face;
wherein said first and second cameras are operative to obtain the visual and thermal images, respectively, of said user of said cart only after said computer processor having received a spoken command to commence opening said at least one locking compartment.

8. The medications or anesthesia cart according to claim 7, wherein upon said spoken command, said first and second cameras are respectively operated sequentially within a brief predetermined length of time that is less than a time required to substitute a false thermal face for a false image of a face for the user for either of said first or second cameras.

9. The medications or anesthesia cart according to claim 8, wherein said brief predetermined length of time is substantially one second.

* * * * *